United States Patent
Jinwal et al.

(10) Patent No.: US 9,750,753 B1
(45) Date of Patent: Sep. 5, 2017

(54) METHOD OF TREATING DISEASES ASSOCIATED WITH LRRK2 MUTATION USING HEXACHLOROPHENE

(71) Applicants: Umesh K. Jinwal, Tampa, FL (US); Malathi Narayan, Tampa, FL (US)

(72) Inventors: Umesh K. Jinwal, Tampa, FL (US); Malathi Narayan, Tampa, FL (US)

(73) Assignee: University of South Florida, Tampa, FL (US)

( * ) Notice: Subject to any disclaimer, the term of this patent is extended or adjusted under 35 U.S.C. 154(b) by 115 days.

(21) Appl. No.: 14/742,116

(22) Filed: Jun. 17, 2015

Related U.S. Application Data

(60) Provisional application No. 62/013,254, filed on Jun. 17, 2014.

(51) Int. Cl.
| | | |
|---|---|---|
| *A61K 31/05* | (2006.01) | |
| *A61K 31/58* | (2006.01) | |
| *A61K 31/122* | (2006.01) | |

(52) U.S. Cl.
CPC .............. *A61K 31/58* (2013.01); *A61K 31/05* (2013.01); *A61K 31/122* (2013.01)

(58) Field of Classification Search
None
See application file for complete search history.

(56) References Cited

U.S. PATENT DOCUMENTS

| 8,669,048 B2 * | 3/2014 | Reijo Pera | 435/29 |
| 2011/0111014 A1 | 5/2011 | Langston | |
| 2013/0102586 A1 * | 4/2013 | Vankayalapati | C07D 471/04 514/210.21 |

OTHER PUBLICATIONS

Eleuteri S. et al., Novel therapeutic strategy for neurodegeneration by blocking Aβ seeding mediated aggregation in models of Alzheimer's disease, Neurobiology of Disease, 2015, 74:144-157.

Gillardon, F. et al. Parkinson's Disease-Linked Leucine-Rich Repeat Kinase 2(R1441G) Mutation Increases Proinflammatory Cytokine Release From Activated Primary Microglial Cells and Resultant Neurotoxicity, Neuroscience 2012, 208, 41-48.

Hanig, J.P. et al., Protection with butylated hydroxytoluene and other compounds against intoxication and mortality caused by hexachlorophene, Fd Chem. Toxic., 1984, 22(3):185-189.

Ho, K.E. Rosenbusch and A. Kortholt, The Potential of Targeting LRRK2 in Parkinson's Disease, A Synopsis of Parkinson's Disease, Dr. Abdul Qayyum Rana (Ed.), ISBN: 978-953-51-1229-7, InTech, 2014, pp. 1-32.

Liu, Z. et al., The role of LRRK2 in inflammatory bowel disease, Cell Research, 2012, 22:1092-1094.

Manzoni, C., LRRK2 and autophagy: a common pathway for disease, Biochem Soc Trans, 2012, 40(5):1147-1151.

Narayan, M. et al., Withaferin A regulates LRRK2 levels by interfering with the Hsp90-Cdc37 chaperone complex, Current Aging Science, 2015, 8(1):1-7.

Nuytemans K., et al., Genetic Etiology of Parkinson Disease Associated with Mutations in SNCA, APRK2, PINK1, PARK7 and LRRK2 Genes: A Mutation Update, Human Mutation, 2010, 31(7): 763-780.

Saunders- Pullman, R. et al.; LRRK2 G20195 Mutations are associated with an increased cancer risk in Parkinson Disease, Movement Disorders, 2010, 25(15), 2536-2541.

Wang, D. et al., Association of the LRRK2 genetic polymorphisms with leprosy in Han Chinese from Southwest China, Genes Immun., 2015, 16(2):112-119.

Yapar, K. et al., Protective effects of L-carnitine on the hexachlorophene-induced neurotoxicity and oxidative stress in mice, Revuede Medecine Veterinaire, 2007, 158(12):607-612.

* cited by examiner

*Primary Examiner* — Samantha Shterengarts
(74) *Attorney, Agent, or Firm* — Michele L. Lawson; Smith & Hopen, P.A.

(57) ABSTRACT

A method of treating a disease associated with mutation of LRRK2 protein is presented herein. It was found that administering hexachlorophene to cells expressing endogenous LRRK2 or overexpressing wild-type or mutant LRRK2 reduced the total LRRK2 level in the cells.

12 Claims, 2 Drawing Sheets

Figure 1A-C

METHOD OF TREATING DISEASES ASSOCIATED WITH LRRK2 MUTATION USING HEXACHLOROPHENE

CROSS REFERENCE TO RELATED APPLICATIONS

This application is a nonprovisional of and claims priority to U.S. Provisional Patent Application No. 62/013,254, entitled "Method of Treating Diseases Associated With LRRK2 Mutation Using Hexachlorophene", filed Jun. 17, 2014, the entire contents of which is herein incorporated into this disclosure.

FIELD OF INVENTION

This invention relates to treating diseases associated with mutations in the LRRK2 protein. Specifically, the invention describes methods of treating diseases such as Parkinson's disease and Crohn's disease using hexachlorophene.

BACKGROUND OF THE INVENTION

Leucine-rich Repeat Kinase 2 (LRRK2) is a gene belonging to the PARK family of genes. LRRK2 is a complex 285 kD protein containing a RAS of complex GTPase domain (ROC), a C-terminal of ROC domain (COR), and a Ser/Thr kinase domain, in addition to three potential protein interaction domains: an ankyrin domain (ANK), leucine-rich repeats (LRR), and WD40 repeats. Based on the presence of these catalytic domains and scaffold domains, it has been speculated that LRRK2 may be involved in the assembly of multiprotein signaling complexes. (Gardet, A. et al., LRRK2 is involved in the IGN-γ response and host response to pathogens, *J Immunol.*, 2010, 185(9):5577-5585)

The LRRK2 gene is active in the brain and other tissues throughout the body. A number of biological functions have been ascribed to LRRK2, ranging from regulating protein translation through phosphorylating E4-BP, controlling microRNA-mediated translational repression, contributing to neurite extension through interaction with Rac1, regulating autophagy by some unknown mechanism, accelerating neurite degeneration induced by α-synuclein. (Liu, Z. et al., The role of LRRK2 in inflammatory bowel disease, *Cell Research*, 2012, 22:1092-1094).

The LRRK2 gene provides instructions for making the LRRK2 protein (also called dardarin). One segment of the dardarin protein is called a leucine-rich region because it contains a large amount of a protein building block (amino acid) known as leucine. Proteins with leucine-rich regions appear to play a role in activities that require interactions with other proteins, such as transmitting signals or helping to assemble the cell's structural framework (cytoskeleton). Other parts of the dardarin protein are also thought to be involved in protein-protein interactions.

Additional studies indicate that dardarin has an enzyme function known as kinase activity. Proteins with kinase activity assist in the transfer of a phosphate group (a cluster of oxygen and phosphorus atoms) from the energy molecule ATP to amino acids in certain proteins. This phosphate transfer is called phosphorylation, and it is an essential step in turning on and off many cell activities. Dardarin also has a second enzyme function referred to as a GTPase activity. This activity is associated with a region of the protein called the ROC domain. The ROC domain may help control the overall shape of the dardarin protein.

Parkinson's disease (PD) is the second most common neurodegenerative disease that affects more than 5 million people, accounting to 1-2% of the population worldwide. It is characterized by the loss of dopaminergic neurons in the substantia nigra associated with the formation of fibrillar aggregates that are composed of α-synuclein and other proteins. PD is clinical characterized by four major symptoms; tremor, bradykinesia, rigidity and postural instability. Initially PD was considered sporadic, however genetic studies in patients families revealed mutations that are segregating with PD. In addition to environmental factors, mutations within 6 loci (SNCA, LRRK2, PRKN, DJ1, PINK1 and ATP13A2) have been clearly demonstrated to be causative to familial PD. Among them, SNCA and LRRK2 mutations cause autosomal dominant forms of PD. LRRK2 has been found to be thus far the most frequent cause of late-onset PD. The identification of missense mutations in LRRK2 has redefined the role of genetic variation in PD susceptibility. The mutations are found in 5-6% of patients with familial PD, and also have been implicated with sporadic PD. (F. Y. Ho, K. E. Rosenbusch and A. Kortholt (2014). The Potential of Targeting LRRK2 in Parkinson's Disease, A Synopsis of Parkinson's Disease, Dr. Abdul Qayyum Rana (Ed.), ISBN: 978-953-51-1229-7, InTech, DOI: 10.5772/57362).

Researchers have identified more than 100 LRRK2 gene mutations in families with late-onset Parkinson disease (the most common form of the disorder, which appears after age 50). These mutations replace single amino acids in the dardarin protein, which affects the protein's structure and function. It is unclear how LRRK2 gene mutations lead to the movement and balance problems characteristic of Parkinson disease (PD).

The first two publications of PD associated mutations in LRRK2 described four different pathogenic missense mutations segregating in families of European and North-American origin. Subsequent mutation analyses identified about 80 discrete missense mutations in over a 1,000 families and sporadic patients worldwide. This corresponds to about 50% of all reported unrelated carriers of mutations in the five major genes, making LRRK2 the most frequently mutated PD gene so far. The 80 missense mutations are located over the entire LRRK2 protein and affect all predicted functional domains. Some mutations, though, have much higher frequencies than others, for example, p.Gly2019Ser and mutations altering codon Arg1441. (Nuytemans K., et al., Genetic Etiology of Parkinson Disease Associated with Mutations in SNCA, APRK2, PINK1, PARK7 and LRRK2 Genes: A Mutation Update, *Human Mutation*, 2010, 31(7): 763-780).

An important observation is that the LRRK2 mutation frequency is seemingly dependent on the ethnicity of the population analyzed. Studies in Caucasians have found that the GLY2019Ser mutation in LRRK2 is a relatively common cause of familial Parkinson's disease and may also be a cause in sporadic Parkinson's disease. For example, the most frequent mutation with a strong founder effect—p.Gly2019Ser—was reported worldwide with an average frequency of 1% in PD patients (Paisan-Ruiz, 2009). But, in Arab Berber and Ashkenazi Jewish populations the p.Gly2019Ser frequency was significantly higher (20 and 40%, respectively) (Lesage et al., 2006; Ozelius et al., 2006), whereas in the first comprehensive screening of a Belgian population, p.Gly2019Ser was apparently absent. (Nuytemans 2010)

A mutation that replaces the amino acid arginine with the amino acid glycine at protein position 1441 (written as Arg1441Gly or R1441G) is a relatively common cause of Parkinson disease in the Basque region between France and Spain. The protein name dardarin comes from the Basque word "dardara," which means tremor, a characteristic feature of Parkinson disease.

Studies of several different populations from around the world revealed a common LRRK2 gene mutation in 3 to 7 percent of familial Parkinson disease cases. This mutation replaces the amino acid glycine with the amino acid serine at protein position 2019 (written as Gly2019Ser or G2019S). The incidence of the Gly2019Ser mutation in familial cases is highest among Arabs from North Africa and people of Ashkenazi (eastern and central European) Jewish ancestry, and it is lowest in Asian and northern European populations. This particular mutation has also been reported in 1 to 3 percent of sporadic Parkinson disease cases, in which there is no family history of the disease.

Studies in Chinese and Japanese populations have identified an LRRK2 gene mutation that occurs more frequently in people with Parkinson disease than in people without the disease. This mutation replaces the amino acid glycine with the amino acid arginine at protein position 2385 (written as Gly2385Arg or G2385R). This mutation appears to increase the risk of Parkinson disease among people in these populations.

In contrast to other PD genes, LRRK2 mutations have a relatively high frequency of up to 2% in sporadic, late-onset PD patients which makes LRRK2 the most frequently mutated gene of the five major PD genes.

Typically, patients carrying LRRK2 missense mutations present with clinical features similar to those of idiopathic PD, that is, asymmetrical late onset, bradykinesia, rigidity, tremor, and good L-dopa response. The incidence of tremor, however, seems to be elevated in LRRK2 carriers indicating that LRRK2 mutations most likely lead to tremor-dominant disease. (Nuytemans 2010)

It has been suggested that LRRK2 is an IFN-γ target gene that is involved in signaling pathways that are relevant to Crohn's disease (CD) pathogenesis. LRRK2 is highly expressed after IFN-γ stimulation. Crohn's disease is a chronic inflammatory bowel disease (IBD) that is believed to result from dysregulated immune response to commensal intestinal microbiota. The single nucleotide polymorphism (SNP) rs11175593, located in a noncoding region on chromosome 12, is one of the loci identified as a risk factor for CD. LRRK2 expression has been shown to be increased in intestinal tissues upon Crohn's disease inflammation. In inflamed intestinal tissues, LRRK2 is detected in the lamina propria macrophages, B-lymphocytes, and CD103-positive dendritic cells. Furthermore, LRRK2 expression enhances NF-κB-dependent transcription, suggesting its role in immune response signaling. (Gardet 2010)

Recent reports suggest a functional association between LRRK2 and autophagy. The LRRK2 locus has been linked to other diseases such as leprosy and cancer. (Manzoni, C., LRRK2 and autophagy: a common pathway for disease, *Biochem Soc Trans*, 2012, 40(5): 1147-51)

Leprosy is a chronic infectious and neurological disease that is caused by infection of *Mycobacterium leprae* (*M. leprae*). Several LRRK2 variants have been found to be significantly associated with leprosy among the Han Chinese population. (Wang, D. et al., Association of the LRRK2 genetic polymorphisms with leprosy in Han Chinese from Southwest China, *Genes Immun.*, 2015, 16(2):112-9)

An increased incidence of certain non-skin cancers such as renal, breast, lung and prostate cancers, as well as acute myelogenous leukemia (AML), has been reported in Parkinson's disease patients with the LRRK2 G2019S mutation (Saunders-Pullman, R. et al.; Movement Disorders, 2010, 25(15), 2536-2541).

Hexachlorophene (also referred to herein as B10), an organochlorine compound, specifically a chlorinated bisphenol, was widely used as an effective antiseptic for topical applications until the 1970s (Kimbrough, 1971; Pilapil, 1966). It has been found to cause toxicity in animal models (Kimbrough and Gaines, 1971; Thorpe, 1967), and its use was discontinued due to the severity of side effects in human beings. It is generally prepared by the condensation of 2 moles of 2,4,5-trichlorophenol with 1 mole formaldehyde in the presence of concentrated sulfuric acid. B10 can be absorbed into the body through the skin or by ingestion. Oral toxicity studies in rats show an $LD_{50}$=66 mg/kg.

B10 has been shown to inhibit the Wnt-β-catenin signaling pathway in B lymphoma cells (Min et al., 2009), and recently to inhibit amyloid beta (Aβ) fibril formation and protect primary neuronal cultures from Aβ-induced toxicity (Eleuteri et al., 2014).

In overcoming the toxicity of hexachlorophene (B10) administration alone, another group found that pre-treatment with antioxidants, such as butylated hydroxytoluene (BHT) and ethoxyquin, prior to administration of B10 protects rats from toxicity induced by B10. BHT and ethoxyquin are both free-radical scavengers that prevent lipid peroxidation. In addition, this group also found that agents, such as phenobarbital and SKF-525A (2-diethylaminoethyl-2,2-diphenylvalerate-Hcl), also lessened toxicity when administered prior to B10. The pre-treatment agents were administered daily for at least 3 days prior to administration of B10. It was noteworthy that the protective effect of SKF-525A only occurred upon oral administration of the drug, not ip administration. It was suggested that this effect may occur because a higher SKF-525A is a cytochrome P450 inhibitor which is known to potentiate barbiturate effects and phenobarbital is a barbiturate itself (Hanig, J. P. et al., Protection with butylated hydroxytoluene and other compounds against intoxication and mortality caused by hexachlorophene, *Fd Chem. Toxic.*, 22(3):185-189)

A different group also noted that pre-treatment with the antioxidant L-carnitine also protected rats from the toxicity of B10. (Yapar, K. et al., Protective effects of L-carnitine on the hexachlorophene-induced neurotoxicity and oxidative stress in mice, *Revuede Medecine Veterinaire*, 2007, 158(12):607-612)

In addition to hexachlorophene, it has been previously found that Heat Shock Protein 90 (Hsp90) inhibitors such as withaferin A (WA) and celestrol also may be used to decrease LRRK2 levels in cells. While both compounds alone reduced LRRK2 levels in cells in a dose and time dependent manner, it was found that treatment with WA in the presence of celastrol enhanced the clearance of LRRK2 in an additive manner. In light of the results, it is suggested that LRRK2 levels can be regulated by targeting the Hsp90-Cdc37 complex. (Narayan, M. et al., Withaferin A regulates LRRK2 levels by interfering with the Hsp90-Cdc37 chaperone complex, *Current Aging Science*, 2015, 8(1):1-7). Use of Hsp90 inhibitors, such as WA and celastrol, in combination with a drug such as hexachlorophene or its derivatives, could enhance reduction and/or inhibition of LRRK2 protein levels in cells and thus provide a potential treatment for disease associated with LRRK2 mutations.

Given the limited options that exist for treatment of diseases associated with LRRK2 mutations, what is needed is an LRRK2 inhibitor that is capable of reducing LRRK2 expression in patients suffering from diseases associated with LRRK2 mutations or overexpression.

SUMMARY OF INVENTION

The inventors have developed a novel method of treating diseases that are linked to the mutation of LRRK2 protein such as Parkinson's disease and Crohn's disease.

The inventors have found that treatment of cells expressing endogenous LRRK2 protein or overexpressing wild-type or mutant LRRK2 protein with hexachlorophene dramatically reduces both endogenous and overexpressed wild-type and mutant LRRK2 levels in cell models. These results indicate that hexachlorophene may serve as a potential therapeutic option for treatment of Parkinson's disease and Crohn's disease as well as other diseases involving mutation of the LRRK2 protein.

A method of treating diseases associated with LRRK2 mutations is presented comprising administering a therapeutically effective dose of an LRRK2 inhibitor to a patient in need thereof. The diseases treated may include Parkinson's disease (PD); autoimmune disorders such as Crohn's disease including inflammatory bowel syndrome (IBS) and ulcerative colitis, leprosy, rheumatoid arthritis and psoriasis; and cancers such as brain, skin, renal, breast, lung and prostate cancers, as well as acute myelogenous leukemia (AML). The LRRK2 inhibitor may be hexachlorophene.

In some embodiments, hexachlorophene may be administered concomitantly with a drug selected from the group consisting of withaferin and celastrol In some embodiments, the LRRK2 inhibitor may be encapsulated in a vesicle prior to administration to the patient where the vesicle is selected from the group consisting of liposomes, niosomes, micelles, multilamellar vesicles, unilamellar vesicles, and polymersomes.

In other embodiments, a pre-administration agent may be administered at a time period prior to administration of the LRRK2 inhibitor. The pre-administration agent may be an antioxidant selected from the group consisting of butylated hydroxytoluene (BHT), ethoxyquin and L-carnitine. Additional pre-administration agents include phenobarbital and SKF-525A. In some embodiments, the pre-administration agent may be administered to the patient at least once per day for at least one day prior to administration of the LRRK2 inhibitor.

A method of reducing expression of LRRK2 in a cell is presented comprising contacting the cell with a therapeutically effective amount of hexachlorophene. In some embodiments, hexachlorophene is administered concomitantly with a Hsp90 inhibitor. The Hsp90 inhibitor may be withaferin A (WA) or celastrol.

A method of inhibiting LRRK2 activity in a cell is also presented comprising contacting the cell with a therapeutically effective amount of hexachlorophene. In some embodiments, hexachlorophene is administered concomitantly with a Hsp90 inhibitor. The Hsp90 inhibitor may be withaferin A (WA) or celastrol.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
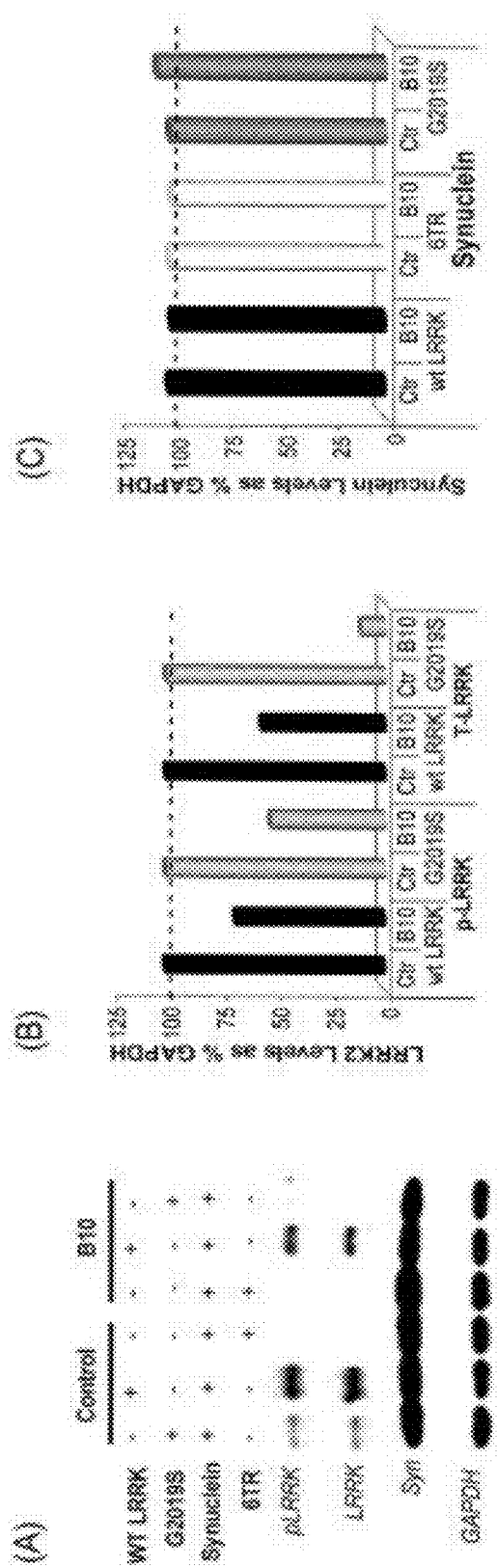
FIG. 1A-C is a series of images depicting hexachlorophene (1 µM) selectively reduces overexpressed wild-type and mutant (G2019S) LRRK2 and does not affect synuclein in the HeLa cells.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Definitions

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used in the specification and claims, the singular form "a", "an" and "the" include plural references unless the context clearly dictates otherwise.

"Patient" is used to describe an animal, preferably a human, to whom treatment is administered, including prophylactic treatment with the compositions of the present invention.

The "therapeutically effective amount" for purposes herein is thus determined by such considerations as are known in the art. A therapeutically effective amount of the compositions or any combination thereof is that amount necessary to provide a therapeutically effective result in vivo or in vitro, including, but not limited to, total prevention of (e.g., protection against) and to improved survival rate or more rapid recovery, or improvement or elimination of symptoms associated with neurodegenerative disorders, or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

The term "vesicle" or "nanoparticle vesicle" as used herein refers to small bubble-like vesicles that may be used as a drug-delivery system. The vesicles may be comprised of lipids such as phospholipids, cholesterol and non-ionic surfactants, copolymers, biodegradable and biocompatible polymers such as chitosin, PLA, PLGA, and starch. Drugs may be encapsulated within the nanoparticle vesicle to enhance bioavailability of the drug. Nanoparticle vesicles include, but are not limited to, liposomes, niosomes, micelles, multilamellar vesicles, unilamellar vesicles, and polymersomes. The nanoparticle vesicles can be between 1 nm and 250 nm (generally over 100 nm) and can encapsulate the drug to be delivered. In some embodiments, these may vesicles self-assemble during preparation. While the nanoparticle vesicles can range in size, in some embodiments the nanoparticle vesicles may be between 30 nm and 80 nm so as to be able to pass the blood-brain barrier.

"Pre-treatment agent" or "pre-administration agent" as used herein refers to a first agent that is administered, in vitro or in vivo, at a time period prior to the administration of a second agent. In some embodiments, the first agent is an a composition that reduces at least one adverse effect of the second agent, including reducing toxicity of the second agent or enhancing the treatment effect of the second agent, in some instances this enhancement may be in an additive or synergistic manner. In some embodiments, the first agent is an agent which reduces the toxicity of hexachlorophene, as the second agent, including, but not limited to, butylated hydroxytoluene (BHT), ethoxyquin, L-carnitine, phenobarbital, and SKF-525A.

"Administration" or "administering" is used to describe the process by which the compounds of the present invention, or any combination thereof, are delivered to a patient. The composition may be administered in various ways including parenteral (referring to intravenous and intraarterial and other appropriate parenteral routes), intratheceal, intraventricular, intracisternal, intranigral, oral, transdermally, subcutaneously, and other routes that allow the composition to contact neurons. The compositions of the invention may be administered independently or in combination with other compounds. Administration will often depend on the disease and level of progression in the afflicted system.

"Active agent" as used herein is defined as a substance, component or agent that has measurable specified or selective physiological activity when administered to an individual in a therapeutically effective amount. Examples of active agents as used in the present invention include LRRK2 inhibitors such as hexachlorophene. At least one active agent is used in the compositions of the present invention.

The terms "pharmaceutical compositions", "drugs", "agents" and "compounds" are used interchangeably herein to refer to a molecule, a group of molecules, a complex or substance containing an active agent that is administered to a subject for diagnostic, therapeutic, preventative, medical, or veterinary purposes. Included are externally and internally administered topical, localized and systemic human and animal pharmaceuticals, treatments, remedies, nutraceuticals, biologicals, and diagnostics, including preparations useful in clinical and veterinary screening, prevention, prophylaxis, healing, wellness, detection, imaging, diagnosis, therapy, surgery, monitoring, and the like.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations which can be used in connection with the subject invention.

For ease of administration, the subject compounds may be formulated into various pharmaceutical forms. As appropriate compositions there may be cited all compositions usually employed for systemically or topically administering drugs. To prepare the pharmaceutical compositions of this invention, the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules often represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g. as a transdermal patch, as a spot-on or as an ointment.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition. Eleuteri et al. found 50% brain permeability of hexachlorophene at a dose of about 10 mg/kg for a transgenic TDP43 mouse model. (Eleuteri S. et al., Novel therapeutic strategy for neurodegeneration by blocking Aβ seeding mediated aggregation in models of Alzheimer's disease, *Neurobiology of Disease*, 2015, 74:144-157). Based on these results, an exemplary in vivo dosage is about 10 mg/kg. This dose can be adjusted downward to establish a minimum dosage in vivo and can be adjusted upwards to establish a maximum dosage in vivo for the present invention as is known by those of skill in the art. While the model used in Eleuteri is a TDP-43 mouse model, its implications for dosage are also applicable to treatment of diseases associated with LRRK2 mutations.

The compounds used in the present invention may be administered individually, or in combination with or concurrently/concomitantly with one or more other compounds used to treat the diseases listed herein.

"Leucine-Rich Repeat Kinase 2 (LRRK2) associated diseases" as used herein refers to diseases having, as one of its causative agents, a mutation in the LRRK2 gene/protein or an overexpression of the LRRK2 protein. Mutated LRRK2 genes are associated with an increased risk of diseases including, but not limited to, Parkinson's disease (PD); autoimmune disorders such as Crohn's disease including inflammatory bowel syndrome (IBS) and ulcerative colitis, leprosy, rheumatoid arthritis and psoriasis; and cancers such as brain, skin, renal, breast, ling and prostate cancers, as well as acute myelogenous leukemia (AML).

"LRRK2 inhibitors" as used herein refers to pharmaceutical compositions such as small molecule inhibitors that inhibit LRRK2 expression and/or decrease protein levels of LRRK2 protein. An example of such an inhibitor is hexachlorophene and its derivatives. Additional examples of inhibitors that may be used include, but are not limited to, Hsp90 inhibitors such as withaferin A and celastrol. These Hsp90 inhibitors, such as withaferin A and celastrol, may be administered concomitantly with hexachlorophene in some embodiments.

LRRK2 has been found in many areas of the body such as in various regions of the brain as well as in the heart, lung, spleen and kidney. LRRK2 protein has a complex structure with many independent domains. Independent domains that have been established for the LRRK2 protein include an ankyrin-like (ANK) domain, a leucine-rich repeat (LRR) domain, a Ras (renin-angiotensin system) of complex (ROC) domain, a C-terminal of ROC (COR) domain, a kinase (Kinase) domain and a C-terminal WD40 domain. The ROC domain binds guanosine triphosphate (GTP) and the COR domain may be a regulator of the ROC domain's GTPase activity.

Mutations in LRRK2 protein have been shown to be one of the causative agents for the pathogenesis of Parkinson's disease and Crohn's disease. Over 20 LRRK2 mutations have been associated with autosomal-dominant PD. The R1441 C, R1441 G, R1441 H, Y1699C, G2019S, 12020T and N1437H missense mutations are known to be pathogenic. The LRRK2 R1441 G mutation has been shown to increase the release of proinflammatory cytokines (higher levels of TNF-α, IL-1β, IL-12 and lower levels of IL-10) in microglial cells from transgenic mice and thus may result in direct toxicity to neurons. (Gillardon, F. et al. Neuroscience 2012, 208, 41-48). The most common of the LRRK2 mutations, G2019S, is present in more than 85% of PD patients carrying LRRK2 mutations. This mutation, which is present in the LRRK2 kinase domain, leads to an enhancement of LRRK2 kinase activity. In the human brain, LRRK2 expression is highest in the same regions of the brain that are impacted by PD, and LRRK2 is found in Lewy Bodies, a hallmark of PD.

Recent studies have indicated that LRRK2 may play a role in the pathogenesis of inflammatory bowel diseases such as Crohn's disease. LRRK2 expression has been found to be enriched in human immune cells and increased in intestinal tissues that are inflamed during Crohn's Disease. (Gardet 2010).

Given the lack of therapies for diseases having LRRK2 mutations, the inventors investigated the therapeutic potential of using an LRRK2 inhibitor such as hexachlorophene to treat diseases such as PD and CD.

Methods

Figure 2:
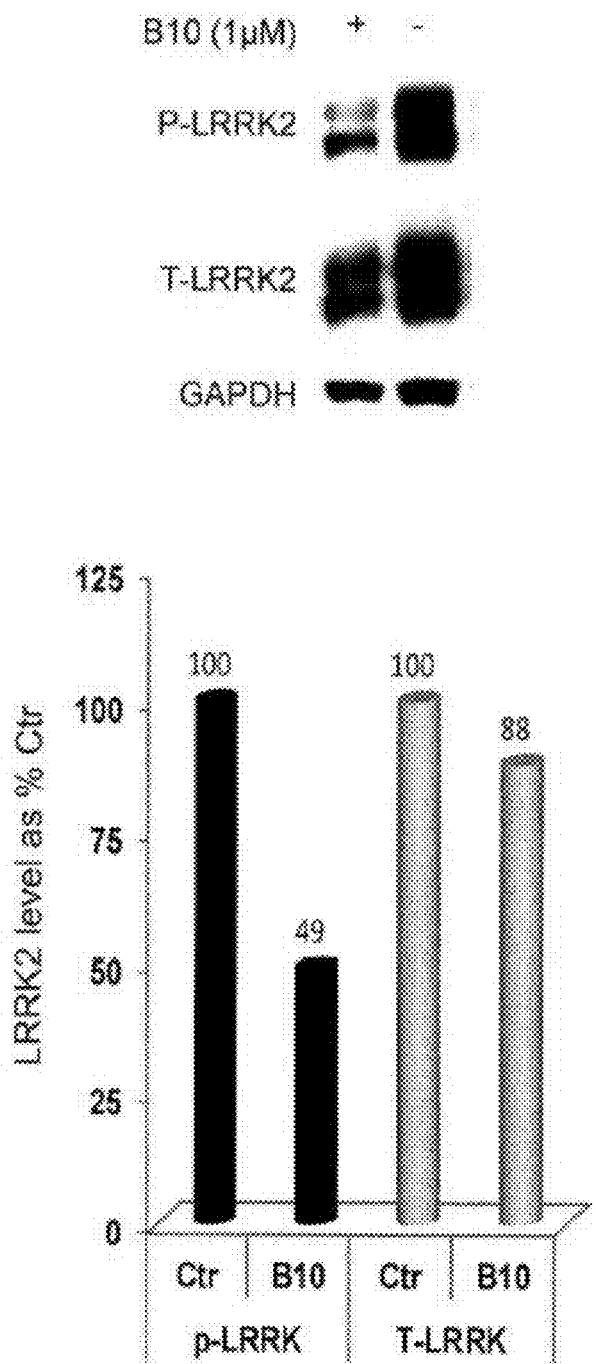
FIG. 2 is a series of images depicting hexachlorophene reduces endogenous pLRRK2. As shown in the figures, treatment of N9 cells expressing endogenous LRRK2 with hexachlorophene (1 µM) for 24 hours reduced the expression of LRRK2.

HeLa cells overexpressing wild-type or mutant human LRRK2 protein and N9 cells expressing endogenous LRRK2 protein were treated with hexachlorophene (labeled as B10 in FIGS. 1 and 2) for 24 hours.

HeLa cells were grown in DMEM with 10% FBS and 1% penicillin and streptomycin. Cells were transfected with constructs for LRRK2 and the G2019S mutant using Lipofectamine 2000. HeLa cells were used due to the ease of transfection with LRRK2 and its mutants.

N9 cells were grown in DMEM supplemented with 10% FBS, 1% penicillin and streptomycin, and 2% L-glutamine. N9 cells were used because they express high levels of endogenous LRRK2. They are very difficult to transfect and were only used to study the effect of hexachlorophene on wild-type LRRK2.

Samples were harvested by using MPER mammalian extraction buffer (Pierce, Thermo Scientific) containing protease and phosphatase inhibitors. After protein estimation using a BCA kit (Pierce, Thermo Scientific), equal amounts of protein from each sample was subjected to gel electrophoresis and western blotting. Phospho (p-) and Total (T-) LRRK2 (abcam) and GAPDH (Meridian Life Sciences) antibodies were used to detect phospho and total LRRK2 and GAPDH, respectively. Analysis of changes in the LRRK2 level was performed using Scion Image software.

The inventors found that hexachlorophene has a maximal effect on LRRK2 levels over a 24-hour period. N9 and HeLa cells tolerate the drug well at the dosages used as evidenced by minimal amounts of cell death as determined by using an LDH release assay as described in Narayan et al. 2015, herein incorporated by reference. It was found that treatment with hexachlorophene decreased levels of total LRRK2 protein as well as mutant LRRK2.

Prophetic Example

The inventors administer a range of dosages of hexachlorophene or one of its derivatives to a transgenic animal, such as a rat, to determine the optimal dosage as well as a range of dosages that are compatible with the organism. The time period between administrations is also calculated to determine a dosing schedule. In some embodiments, the hexachlorophene is administered either after pre-treatment/pre-administration with an antioxidant or other agent which has been shown to reduce the toxicity of hexachlorophene. In some embodiments, the pre-administration agent is butylated hydroxytoluene (BHT), ethoxyquin, L-carnitine, phenobarbital, or SKF-525A. The pre-administration agent is administered to the patient daily for a time period of at least one day prior to administration of the hexachlorophene.

In an alternative embodiment, no pre-administration agent is administered but the hexachlorophene is encapsulated in a vesicle such as liposomes, niosomes, micelles, multilamellar vesicles, unilamellar vesicles, and polymersomes prior to administration to the patient. Encapsulation in a vesicle ensures targeting of the drug to the correct tissues and controlled release over time.

In still another embodiment, another agent, such as withaferin or celestrol, may be administered concomitantly with the hexachlorophene, or its derivatives, with this other agent being capable of limiting the toxicities of hexachlorophene.

Conclusions

Overall the results suggest that treatment with hexachlorophene reduces both endogenous and overexpressed phospho and total LRRK2 (both wild-type and mutant) compared to vehicle DMSO control (Ctr). These results indicate that hexachlorophene (B10) may serve as a potential treatment option for Parkinson's disease, Crohn's disease and other related disorders.

The previously noted toxicities of hexachlorophene can be overcome through the use of encapsulation technologies used to encapsulate the drug within a vesicle or through the administration of a pre-administration agent such as an antioxidant as disclosed herein. In addition, a drug such as withaferin or celestrol may be concomitantly administered with hexachlorophene.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of treating a disease characterized by mutation of LRRK2 protein in a patient in need thereof comprising administering a therapeutically effective amount of hexachlorophene, wherein the hexachlorophene is administered concomitantly with a drug selected from the group consisting of withaferin A and celastrol.

2. The method of claim 1, wherein the disease is Parkinson's disease.

3. The method of claim 1, wherein the disease is an autoimmune disease selected from the group consisting of Crohn's disease, leprosy, rheumatoid arthritis and psoriasis.

4. The method of claim 1, further comprising encapsulating the hexachlorophene in a vesicle prior to administration to the patient.

5. The method of claim 4, wherein the vesicle is selected from the group consisting of liposomes, niosomes, micelles, multilamellar vesicles, unilamellar vesicles, and polymersomes.

6. The method of claim 1, further comprising administering a pre-administration agent at a time period prior to administration of the hexachlorophene.

7. The method of claim 6, wherein the pre-administration agent is an antioxidant.

8. The method of claim 7, wherein the antioxidant is selected from the group consisting of butylated hydroxytoluene (BHT), ethoxyquin and L-carnitine.

9. The method of claim 6, wherein the pre-administration agent is selected from the group consisting of butylated hydroxytoluene (BHT), ethoxyquin, L-carnitine, phenobarbital, or SKF-525A.

10. The method of claim 6, wherein the pre-administration agent is administered to the patient at least once per day for at least one day prior to administration of the hexachlorophene.

11. A method of reducing LRRK2 protein expression levels in a cell comprising contacting the cell with a therapeutically effective amount of hexachlorophene, further comprising administering a Hsp90 inhibitor concomitantly with the hexachlorophene, wherein the Hsp90 inhibitor is selected from withaferin A (WA) and celastrol.

12. A method of inhibiting LRRK2 activity in a cell comprising contacting the cell with a therapeutically effective amount of hexachlorophene, further comprising administering a Hsp90 inhibitor concomitantly with the hexachlorophene, wherein the Hsp90 inhibitor is selected from withaferin A (WA) and celastrol.

* * * * *